(12) United States Patent
Wang et al.

(10) Patent No.: US 9,695,231 B2
(45) Date of Patent: Jul. 4, 2017

(54) MONOCLONAL ANTIBODY AGAINST MURAMYL PEPTIDES

(71) Applicant: Agency for Science, Technology and Research, Singapore (SG)

(72) Inventors: Yue Wang, Proteos (SG); Xiaoli Xu, Proteos (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/436,002

(22) PCT Filed: Nov. 1, 2013

(86) PCT No.: PCT/SG2013/000473
§ 371 (c)(1),
(2) Date: Apr. 15, 2015

(87) PCT Pub. No.: WO2014/070117
PCT Pub. Date: May 8, 2014

(65) Prior Publication Data
US 2015/0344547 A1    Dec. 3, 2015

(30) Foreign Application Priority Data

Nov. 1, 2012   (SG) .............................. 201208082-6

(51) Int. Cl.
*C07K 16/12* (2006.01)
*C07K 16/44* (2006.01)
*G01N 33/566* (2006.01)

(52) U.S. Cl.
CPC .......... *C07K 16/12* (2013.01); *C07K 16/1232* (2013.01); *C07K 16/1275* (2013.01); *C07K 16/44* (2013.01); *G01N 33/566* (2013.01); *C07K 2317/92* (2013.01); *G01N 2333/4722* (2013.01)

(58) Field of Classification Search
CPC ................ A61K 2300/00; A61K 39/00; A61K 2039/6012; A61K 31/496; A61K 38/00; C07K 14/59; C07K 14/005; C07K 14/195; C07K 16/12; C07K 16/1232; C07K 16/1275; C07K 16/44; C07K 2317/92; C07K 2319/30; C07K 9/005
See application file for complete search history.

(56) References Cited

U.S. PATENT DOCUMENTS

2009/0258015 A1   10/2009 Wang et al.

FOREIGN PATENT DOCUMENTS

| EP | 0100734 | 2/1984 |
|---|---|---|
| WO | WO-2008024075 | 2/2008 |
| WO | WO-2014/070117 | 5/2014 |

OTHER PUBLICATIONS (Paul, Fundamental Immunology, 3rd Edition, 1993, pp. 292-295, under the heading "Fv Structure and Diversity in Three Dimensions").*
Rudikoff et al (Proc. Natl. Acad. Sci. USA, 79(6):1979-1983, Mar. 1982).*
"International Application No. PCT/SG2013/000473, Written Opinion of the International Searching Authority mailed Jan. 2, 2014", (Jan. 2, 2014), 6 pgs.
"International Application No. PCT/SG2013/000473, International Search Report mailed Jan. 2, 2014", (Jan. 2, 2014), 6 pgs.
Bahr, G. M., et al., "Monoclonal antibodies to the synthetic adjuvant muramyl dipeptide: Characterization of the specificity", Molecular Immunology, vol. 20, Issue 7, Jul. 1983, pp. 745-752, (Jul. 1983), 745-752.
Doublet, Patricia, et al., "The murI Gene of *Escherichia coli* Is an Essential Gene That Encodes a Glutamate Racemase Activity", Journal of Bacteriology, vol. 175, No. 10, May 1993, p. 2970-2979, (May 1993), 2970-2979.
Kettleborough, Catherine A., et al., "Optimization of primers for cloning libraries of mouse immunoglobulin genes using the polymerase chain reaction", European Journal of Immunology, vol. 23, Issue 1, pp. 206-211, Jan. 1993, (Jan. 1993), 206-211.
Klasen, I. S., et al., "The Presence of Peptidoglycan-Polysaccharide Complexes in the Bowel Wall and the Cellular Responses to These Complexes in Crohn's Disease", Clinical Immunology and Immunopathology, vol. 71, Issue 3, Jun. 1994, pp. 303-308, (Jun. 1994), 303-308.
Kool, Jeanette, et al., "Detection of Intestinal Flora-derived Bacterial Antigen Complexes in Splenic Macrophages of Rats", The Journal of Histochemistry and Cytochemistry, vol. 42, No. 11, pp. 1435-1441 (1994), (1994), 1435-1441.
Lee, K. S., et al., "Crystallization and preliminary X-ray crystallographic studies of glutamate racemase from Lactobacillus fermenti", Acta Crystallographica Section F, Structural Biology and Crystallization Communications, vol. 61, Part 2 (Feb. 2005), 199-201, (Feb. 2005), 199-201.
Pope, A. R., et al., "Construction and use of antibody gene repertoires", In: McCafferty J, Hoogenboom R H, Chiswell D J, editors. Antibody engineering: a practical approach. London, United Kingdom: IRL Press; 1996. pp. 1-40, (1996), 1-40.

(Continued)

*Primary Examiner* — Padma V Baskar
(74) *Attorney, Agent, or Firm* — Schwegman Lundberg & Woessner, P.A.

(57) ABSTRACT

Disclosed is an isolated antibody or an antigen-binding fragment thereof. The antibody is capable of binding to a muramyl peptide, or a derivative or an analog or a salt thereof. The muramyl peptide comprises muramic acid and an amino acid selected from the group consisting of alanine, isoglutamine, glutamic acid, and a salt thereof. Also disclosed are methods of producing the antibody, compositions comprising the antibody, methods of treating using the antibody, uses of the antibody, methods of detecting muramyl peptide, an assay for detecting muramyl peptide, an antibacterial agent, hybridomas and kits.

9 Claims, 2 Drawing Sheets

(56) References Cited

OTHER PUBLICATIONS

"European Application No. 13850865.0, Communication pursuant to Rules 70(2) and 70a(2) EPC, dated Oct. 14, 2016", (Oct. 14, 2016), 1 pg.
"European Application No. 13850865.0, Extended European Search Report dated Sep. 27, 2016", (Sep. 27, 2016), 12 pgs.
Inohara, Naohiro, et al., "Host Recognition of Bacterial Muramyl Dipeptide Mediated through NOD2", The Journal of Biological Chemistry, vol. 278 (8), Feb. 21, 2003, 5509-5512, (Jan. 21, 2003), 5509-5512.
Ottaviani, E., et al., "Immunodetection of haemocyte subpopulations by n-acetylmuramic acid antibody in *Planorbarius corneus* (L.) (Gastropoda, Pulmonata)", Histochemical Journal, 21 (11), 675-678 (1989), (Jan. 1, 1989), 675-678.

\* cited by examiner

SEQUENCE LISTING

```
<160> NUMBER OF SEQ ID NOS: 10

<210> SEQ ID NO 1
<211> LENGTH: 624
<212> TYPE: DNA
<213> ORGANISM: Artificial Sequence
<220> FEATURE:
<223> OTHER INFORMATION: Heavy chain

<400> SEQUENCE: 1
atgctggtgg agtctggggg aggcttggtg caacctggag gatccatgaa actctcctgt      60
atagtctcgg gatttacttt cagttattat tggatgtctt gggtccgcca gtctccagag     120 aagggg tttg agtgggttgc tgaaatcaga ttgaaatctg agaattatgc aacaaattat     180
acggagtctg tgaaagggaa gttcaccatc tcaagagatg attccaaaag tcgtctctac     240
ctgcaaatga acagcttagg agctgaggac actggaattt attactgtct aactggttat     300
gcctggtttg cttattgggg ccaagggact ctagtcactg tctctgcagc caaaacgaca     360 ccccc atctg tctatccact ggcccctgga tctgctgccc aaactaactc catggtgacc     420
ctgggatgcc tggtcaaggg ctatttccct gagccagtga cagtgacctg gaactctgga     480
tccctgtcca gcggtgtgca caccttccca gctgtcctgc agtctgacct ctacactctg     540
agcagctcag tgactgtccc ctccagcacc tggcccagcg agaccgtcac ctgcaacgtt     600
gcccacccgg ccagcagcac caag                                            624

<210> SEQ ID NO 2
<211> LENGTH: 531
<212> TYPE: DNA
<213> ORGANISM: Artificial Sequence
<220> FEATURE:
<223> OTHER INFORMATION: Light chain

<400> SEQUENCE: 2
gacgtccaga tgatccagtc tccaaagcgc ctaatctatc tggtgtctaa actggactct      60
ggagtccctg acaggttcac tggcagtgga tcaggaacag atttta cact gaaaatcagc     120 agagtggagg ctgaggattt gggagtttat tactgcgtgc aacatacaca ttttcccacg     180
```

```
ttcggagggg ggaccaagct ggaaataaaa cgggctgatg ctgcaccaac tgtatccatc      240
ttcccaccat ccagtgagca gttaacatct ggaggtgcct cagtcgtgtg cttcttgaac      300
aacttctacc ccaaagacat caatgtcaag tggaagattg atggcagtga acgacaaaat      360
ggcgtcctga acagttggac tgatcaggac agcaaagaca gcacctcaga catgagcagc      420
accctcacgt tgaccaagga cgagtatgaa cgacataaca gctatacctg tgaggccact      480
cacaagacat caacttcacc cattgtcaag agcttcaaca ggaatgagtg t              531
```

```
<210> SEQ ID NO 3
<211> LENGTH: 208
<212> TYPE: PRT
<213> ORGANISM: Artificial Sequence
<220> FEATURE:
<223> OTHER INFORMATION: Heavy chain

<400> SEQUENCE: 3

Met Leu Val Glu Ser Gly Gly Gly Leu Val Gln Pro Gly Gly Ser Met
1               5                   10                  15

Lys Leu Ser Cys Ile Val Ser Gly Phe Thr Phe Ser Tyr Tyr Trp Met
            20                  25                  30

Ser Trp Val Arg Gln Ser Pro Glu Lys Gly Phe Glu Trp Val Ala Glu
        35                  40                  45

Ile Arg Leu Lys Ser Glu Asn Tyr Ala Thr Asn Tyr Thr Glu Ser Val
    50                  55                  60

Lys Gly Lys Phe Thr Ile Ser Arg Asp Asp Ser Lys Ser Arg Leu Tyr
65                  70                  75                  80

Leu Gln Met Asn Ser Leu Gly Ala Glu Asp Thr Gly Ile Tyr Tyr Cys
                85                  90                  95

Leu Thr Gly Tyr Ala Trp Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

<210> SEQ ID NO 4
<211> LENGTH: 177
<212> TYPE: PRT
<213> ORGANISM: Artificial Sequence
<220> FEATURE:
<223> OTHER INFORMATION: Light chain

<400> SEQUENCE: 4

Asp Val Gln Met Ile Gln Ser Pro Lys Arg Leu Ile Tyr Leu Val Ser
1               5                   10                  15

Lys Leu Asp Ser Gly Val Pro Asp Arg Phe Thr Gly Ser Gly Ser Gly
            20                  25                  30

Thr Asp Phe Thr Leu Lys Ile Ser Arg Val Glu Ala Glu Asp Leu Gly
        35                  40                  45
```

```
Val Tyr Tyr Cys Val Gln His Thr His Phe Pro Thr Phe Gly Gly Gly
 50                  55                  60

Thr Lys Leu Glu Ile Lys Arg Ala Asp Ala Ala Pro Thr Val Ser Ile
 65                  70                  75                  80

Phe Pro Pro Ser Ser Glu Gln Leu Thr Ser Gly Gly Ala Ser Val Val
                 85                  90                  95

Cys Phe Leu Asn Asn Phe Tyr Pro Lys Asp Ile Asn Val Lys Trp Lys
                100                 105                 110

Ile Asp Gly Ser Glu Arg Gln Asn Gly Val Leu Asn Ser Trp Thr Asp
                115                 120                 125

Gln Asp Ser Lys Asp Ser Thr Tyr Ser Met Ser Ser Thr Leu Thr Leu
            130                 135                 140

Thr Lys Asp Glu Tyr Glu Arg His Asn Ser Tyr Thr Cys Glu Ala Thr
145                 150                 155                 160

His Lys Thr Ser Thr Ser Pro Ile Val Lys Ser Phe Asn Arg Asn Glu
                165                 170                 175

Cys
```

<210> SEQ ID NO 5
<211> LENGTH: 21
<212> TYPE: DNA
<213> ORGANISM: Artificial Sequence
<220> FEATURE:
<223> OTHER INFORMATION: Heavy chain forward primers 5'->3'

<400> SEQUENCE: 5
atgctggtgg agtctggggg a                                          21

<210> SEQ ID NO 6
<211> LENGTH: 21
<212> TYPE: DNA
<213> ORGANISM: Artificial Sequence
<220> FEATURE:
<223> OTHER INFORMATION: Heavy chain forward primers 5'->3'

<400> SEQUENCE: 6
aagctggtgg aatctggagg a                                          21

<210> SEQ ID NO 7
<211> LENGTH: 21
<212> TYPE: DNA
<213> ORGANISM: Artificial Sequence
<220> FEATURE:
<223> OTHER INFORMATION: Heavy chain Reverse Primer 5'->3'

<400> SEQUENCE: 7
cttggtgctg ctggccgggt g                                          21

<210> SEQ ID NO 8
<211> LENGTH: 24
<212> TYPE: DNA
<213> ORGANISM: Artificial Sequence
<220> FEATURE:
<223> OTHER INFORMATION: Light chain forward primers 5'->3'

<400> SEQUENCE: 8
ccgtttgatt tccagcttgg tgcc                                       24

<210> SEQ ID NO 9
<211> LENGTH: 24
<212> TYPE: DNA

```
<213> ORGANISM: Artificial Sequence
<220> FEATURE:
<223> OTHER INFORMATION: Light chain forward primer 5'->3'

<400> SEQUENCE: 9
ccgtttcagc tccagcttgg tccc                                          24

<210> SEQ ID NO 10
<211> LENGTH: 24
<212> TYPE: DNA
<213> ORGANISM: Artificial Sequence
<220> FEATURE:
<223> OTHER INFORMATION: Light chain reverse primers 5'->3'

<400> SEQUENCE: 10
gacattgagc tcacccagtc tcca                                          24
```

MONOCLONAL ANTIBODY AGAINST MURAMYL PEPTIDES

CROSS-REFERENCE TO RELATED APPLICATIONS

This application is a U.S. national stage application filed under 35 U.S.C. §371 from International Application Serial No. PCT/SG2013/000473, which was filed 1 Nov. 2013, and published as WO 2014/070117 on 8 May 2014, and which claims the benefit of priority of Singapore patent application No. 201208082-6, filed 1 Nov. 2012, which applications and publication are incorporated by reference as if reproduced herein and made a part hereof in their entirety, and the benefit of priority of each of which is claimed herein.

FIELD OF THE INVENTION

The present invention generally relates to the field of immunology and infectious disease. In particular, the present invention relates to antibodies.

BACKGROUND OF THE INVENTION

Bacterial infestation either in the medical field or in commercial non-medical field is unwelcome. To effectively eliminate unwanted bacterial growth, researchers have looked into the basic building blocks of bacteria, such as the cell wall of bacteria. One of the major components of a bacterial cell wall is the peptidoglycans, whose subunits are known as muramyl peptides. Peptidoglycans, which are formed from subunits of muramyl peptides, undergo cycles of assembly and disassembly required for cell wall remodeling during cell growth and division. Muramyl peptides are generated during the disassembly and recycled to construct new peptidoglycans during cell growth and septation. Accordingly, muramyl peptides are constantly released from many bacterial species during proliferation. They are also generated and released when bacterial cells are lysed by phages, antibiotics and host phagocytes.

Many muramyl peptides are potent signaling molecules and have been shown to strongly influence multiple physiological processes in the human host. Biological activities that have been linked to muramyl peptides include adjuvanticity, somnogenicity, pyrogenicity, and toxicity to ciliated epithelial cells. Muramyl peptides have also been associated with a range of human diseases such as sepsis, Crohn's disease, rheumatoid arthritis, asthma, allergy, atopic disorders, multiple sclerosis, pertussis, and gonorrhea. Different types of muramyl peptides carrying different side chains on the muramic acid residues and different amino acid residues in the peptides have distinct activities.

Muramyl peptides impact the human physiology by binding to specific peptidoglycan recognition proteins (PGRPs). Humans have four PGRPs, which are able to directly bind to both Gram-positive and Gram-negative peptidoglycan, and two intracellular peptidoglycan sensors, Nod1 and Nod2 belonging to a large family of pattern recognition receptors that recognize conserved microbe- or pathogen-associated molecular patterns. Nod2 recognizes the muramyl dipeptide N-acetylmuramyl-L-alanyl-D-glutamine, while Nod1 recognize the D-γ-glutamyl-mDAP motif in the peptide. Both Nod1 and Nod2 trigger and regulate the host immune response by activating the transcription factor NF-κB, which in turn switches on the production of proinflammatory cytokines and chemokines and expression of other defense genes. Nod1, Nod2 and NF-κB have been implicated in numerous human diseases.

The human microbiota, which contains 10 to 100 trillion non-pathogenic bacterial cells, constantly produces and secretes large quantities of muramyl peptides. A fraction of these molecules can enter the host circulation system via various mechanisms during the homeostatic state of the host as well as under numerous pathophysiological conditions. In addition to the many established links to human diseases as described above, strong evidence is rapidly accumulating that muramyl peptides released by commensal bacteria play key roles in the development, maintenance and modulation of major human systems such as the immune system, the gastrointestinal barrier, and the brain. Thus, the levels and types of muramyl peptides in the human body are thought to contribute critically to human health and disease predisposition and pathophysiology.

Given the great importance of muramyl peptides in human health and disease, technologies in detecting, quantifying, neutralizing or sequestering these molecules are expected to have broad applications in disease prediction, diagnosis, and treatment. Such technologies can also be used to detect bacterial contamination of medical facilities, reagents, biological products, foods, and beverages.

Monoclonal antibodies raised against muramyl peptides are known in the art. One such antibody mAb2-4, which isotype is IgG2a, has been characterized in detail. However, so far, mAb2-4 has only been known to be used in immunostaining of tissues to detect the presence of peptidoglycan mainly in inflammatory tissues and macrophages. This antibody is not known to be used for detecting peptidoglycan or muramyl peptides in solution by assays such as enzyme-linked immunosorbent assay (ELISA). Additionally, mAb2-4 was found to have very low affinity to muramyl peptides. Inhibition assays using mAb2-4 showed that 50% inhibition of mAb2-4 binding to peptidoglycan by N-acetyl-muramyl-L-alanyl-D-isoglutamine occurred only at concentrations higher than 1 mg/ml. Additionally, structural analysis of antigenic determinant showed that the mAb2-4 antibody recognizes the N-acetylmuramic acid linked to the dipeptide. As many bacterial species do not have the N-acetyl group in the muramic acid residue, mAb2-4 appears to be an antibody that has narrow specificity in recognizing bacterial species.

Another commonly used mouse monoclonal antibody for peptidoglycan is mAb2E9, which was developed by immunizing mice with partially purified peptidoglycan-polysaccharide complexes isolated from the feces of a healthy human. The affinity of this antibody to N-acetylmuramyl-L-alanyl-D-isoglutamine was found to be even lower than mAb2-4, and the antigenic determinant has not been defined. mAb2E9 has been used in immunostaining of tissues but never in ELISA.

Other monoclonal antibodies developed by immunizing mice with peptidoglycan isolated from *Streptococcus mutans* have also been described. Although these antibodies could recognize peptidoglycan prepared from multiple bacterial species including both Gram-positive and Gram-negative ones, the binding of such antibodies are known to be non-specific as they cannot be inhibited by N-acetylmuramyl-L-alanyl-D-isoglutamine and the antigenic determinant is not known.

In view of the low affinity, poorly defined antigenic determinant and narrow specificity of the currently available mouse monoclonal antibodies, there is a need to provide an alternative antibody that recognizes muramyl peptide.

SUMMARY OF THE INVENTION

In a first aspect, there is provided an isolated antibody or an antigen-binding fragment thereof capable of binding to a muramyl peptide, or a derivative or an analog or a salt thereof, comprising muramic acid and an amino acid selected from the group consisting of alanine, isoglutamine, glutamic acid, and a salt thereof.

In a second aspect, there is provided an isolated antibody or an antigen-binding fragment thereof comprising a heavy chain variable domain comprising the amino acid sequence as set forth in SEQ ID NO: 3, or a variant thereof.

In a third aspect, there is provided an isolated antibody or an antigen-binding fragment thereof comprising a light chain variable domain comprising the amino acid sequence as set forth in SEQ ID NO: 4, or a variant thereof.

In a fourth aspect, there is provided an isolated antibody or an antigen-binding fragment thereof comprising a heavy chain variable domain comprising the amino acid sequence as set forth in SEQ ID NO: 3, or a variant thereof, and a light chain variable domain comprising the amino acid sequence as set forth in SEQ ID NO: 4, or a variant thereof.

In a fifth aspect, there is provided an isolated nucleic acid molecule comprising SEQ ID NO: 1 or SEQ ID NO: 2.

In a sixth aspect, there is provided a vector comprising the isolated nucleic acid molecule according to the fifth aspect.

In a seventh aspect, there is provided a host cell comprising the nucleic acid molecule according to the fifth aspect or the vector according to the sixth aspect.

In an eighth aspect, there is provided an isolated cell line that produces the antibody or an antigen-binding fragment thereof as described herein.

In a ninth aspect, there is provided a method of producing an antibody or an antigen-binding fragment thereof as described herein, the method comprising the steps of culturing the host cell according to the seventh aspect or the isolated cell line according to the eighth aspect under suitable conditions and recovering the antibody or antigen-binding fragment thereof.

In a tenth aspect, there is provided a method of producing an antibody or an antigen-binding fragment thereof as described herein, comprising the steps of inoculating a muramyl peptide, or a derivative or an analog or a salt thereof, as described herein into a non-human animal, and isolating antibodies or antigen-binding fragments produced therefrom.

In an eleventh aspect, there is provided a composition comprising an antibody or an antigen-binding fragment thereof as described herein, and a pharmaceutically acceptable carrier.

In a twelfth aspect, there is provided a vaccine comprising a muramyl peptide, or a derivative or an analog or a salt thereof, as described herein.

In a thirteenth aspect, there is provided an immunoconjugate comprising an antibody or an antigen-binding fragment thereof as described herein, covalently attached to: a cytotoxic agent selected from the group consisting of an antibacterial agent, a chemotherapeutic agent, a drug moiety, an antibiotic, a radioisotope, a nucleolytic enzyme, a lysozyme, a proteinase and a lipase; or a capture label; or a detection label selected from the group consisting of fluorescein, rhodamine, dansyl, Lissamine, cyanine, phycoerythrin, Texas Red, and a radionuclide detection label.

In a fourteenth aspect, there is provided a method of prophylactically or therapeutically treating an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-associated disorder, comprising administering to a subject an isolated antibody or an antigen-binding fragment thereof as described herein, a composition according to the eleventh aspect, or an immunoconjugate according the thirteenth aspect.

In a fifteenth aspect, there is provided a method of prophylactically or therapeutically treating a bacterial infection, comprising administering to a subject an isolated antibody or an antigen-binding fragment thereof as described herein, a composition according to the eleventh aspect, or an immunoconjugate according to the thirteenth aspect.

In a sixteenth aspect, there is provided an isolated antibody or an antigen-binding fragment thereof as described herein, a composition according to the eleventh aspect, or an immunoconjugate according to the thirteenth aspect, for use in the prophylactic or therapeutic treatment of an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-associated disorder.

In a seventeenth aspect, there is provided an isolated antibody or an antigen-binding fragment thereof as described herein, a composition according to the eleventh aspect, or an immunoconjugate according to the thirteenth aspect, for use in the prophylactic or therapeutic treatment of a bacterial infection.

In an eighteenth aspect, there is provided use of an isolated antibody or an antigen-binding fragment thereof as described herein, a composition according to the eleventh aspect, or an immunoconjugate according to the thirteenth aspect, in the manufacture of a medicament for prophylactically or therapeutically treating an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-related disorder.

In a nineteenth aspect, there is provided use of an isolated antibody or an antigen-binding fragment thereof as described herein, a composition according to the eleventh aspect, or an immunoconjugate according to the thirteenth aspect, in the manufacture of a medicament for prophylactically or therapeutically treating a bacterial infection.

In a twentieth aspect, there is provided a method of detecting the presence or absence of a muramyl peptide, or a derivative or an analog or a salt thereof, as described herein, in a sample, the method comprising contacting the sample with an isolated antibody or an antigen-binding fragment thereof as described herein, a composition according to the eleventh aspect, or an immunoconjugate according to the thirteenth aspect, and analyzing the sample to determine the presence or absence of the binding product of the muramyl peptide, or a derivative or an analog or a salt thereof, and the isolated antibody or an antigen-binding fragment thereof as described herein.

In a twenty-first aspect, there is provided an assay for detecting a muramyl peptide, or a derivative or an analog or a salt thereof, as described herein, comprising exposing a sample to an antibody or an antigen-binding fragment thereof as described herein, a composition according to the eleventh aspect, or an immunoconjugate according to the thirteenth aspect, and determining the extent of binding of the antibody, or an antigen-binding fragment thereof, the composition or the immunoconjugate to the sample.

In a twenty-second aspect, there is provided a kit for use in a method according to the twentieth aspect, or in an assay according to the twenty-first aspect, comprising an isolated antibody or an antigen-binding fragment thereof as described herein, a composition according to the eleventh aspect, or an immunoconjugate according to the thirteenth aspect, and one or more reagents for determining the presence or absence of the binding product of a muramyl peptide, or a derivative or an analog or a salt thereof, and the isolated antibody or an antigen-binding fragment thereof as described herein.

In a twenty-third aspect, there is provided an antibacterial agent comprising an isolated antibody or an antigen-binding fragment thereof as described herein, a composition according to the eleventh aspect, or an immunoconjugate according to the thirteenth aspect.

In a twenty-fourth aspect, there is provided a hybridoma deposited as Wy-Hyb-2E7 under Accession Number No. PTA-13256 in the American Type Culture Collection (ATCC), Manassas, Va., USA.

In a twenty-fifth aspect, there is provided an antibody comprising the variable heavy and variable light domain sequence of the antibody produced by the hybridoma deposited as Wy-Hyb-2E7 under Accession Number No. PTA-13256 in the American Type Culture Collection (ATCC), Manassas, Va., USA.

BRIEF DESCRIPTION OF THE DRAWINGS

The invention will be better understood with reference to the detailed description when considered in conjunction with the non-limiting examples and the accompanying drawings, in which:

FIG. 2 demonstrates that 2E7, which is an example of the antibody of the present disclosure, recognizes natural peptidoglycan.

FIG. 3 demonstrates that amoxicillin causes a significant increase in blood level of MPs in mice and humans.

DETAILED DESCRIPTION OF THE PRESENT INVENTION

Figure 1:
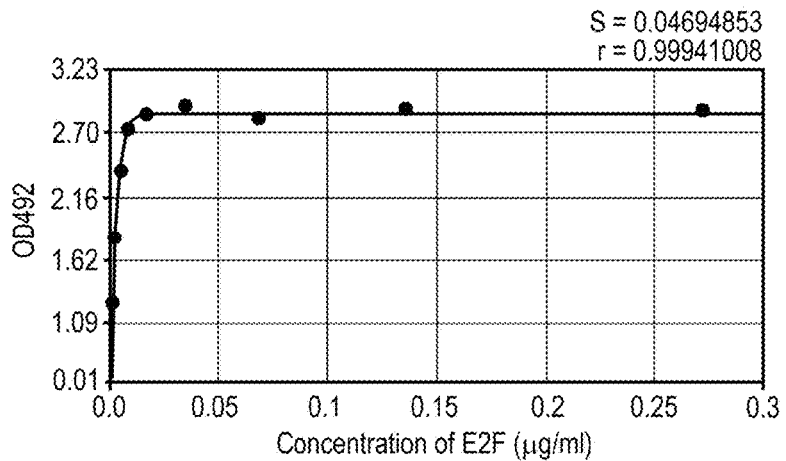
FIG. 1 shows the determination of the Kd value of one example of an antibody as described herein, which is the monoclonal antibody 2E7. To determine the Kd of 2E7 to N-acetylmuramyl-L-alanyl-D-glutamine, the bottom of wells of a 96-well plate was coated with MDP-OVA. 2-fold serial dilutions of 2E7 were added to the wells for incubation. After washes to remove unbound Abs, an anti-mouse-IgG Ab coupled with horseradish peroxidase (HSP) was added. After incubation, unbound secondary Ab was removed by washes and a chromogenic substrate of HSP was added. After reaction, the color intensity in each well was measured using a microtiter plate reader at 492 nm. A binding curve was generated using CurveExpert Basic program (http://www.curveexpert.net) by fitting 2E7 concentrations and OD492 values to the Weibull Model equation $y=a-b*\exp(-C*x\char`\^d)$ using CurveExpert Basic. r: correlation coefficient; s: standard error. Coefficient data: a=2.8768241, b=2.8055033, c=212.44541, and d=0.8659833. $Y_{50}$=1.45, X=0.00131 μg/ml. Kd=0.0131/[150×10$^9$]=8.7 pM (IgG MW=150).

Muramyl peptides are bacterial peptidoglycan that is not known to be present in any other organisms. Accordingly, the inventors of the present disclosure envisage that antibodies that are directed to the various forms of muramyl peptides would be advantageous. Thus, the present invention provides for an isolated antibody that is capable of binding to a muramyl peptide. Accordingly, in a first aspect, there is provided an isolated antibody or an antigen-binding fragment thereof that may be capable of binding to a muramyl peptide, or a derivative or an analog or a salt thereof.

The term "antibody" as used herein refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to initiate an effector activity, or to bind to an antigen in a sample, for example in a solution, in a cell or tissue).

An "isolated antibody," as used herein, refers to an antibody which is substantially free of other antibodies having different antigenic specificities (for instance an isolated antibody that specifically binds to a muramyl peptide is substantially free of antibodies that specifically bind antigens other than a muramyl peptide). An isolated antibody that specifically binds to an epitope, isoform or variant of a muramyl peptide may, however, have cross-reactivity to other related antigens, for instance from other bacterial species (such as a muramyl peptide species homologs).

Moreover, an isolated antibody may be substantially free of other cellular material and/or chemicals.

In one embodiment, the antigen is a muramyl peptide. Muramyl peptide is a hallmark of bacterial peptidoglycan that is formed by parallel arrays of long sugar chains cross-linked by regularly spaced short peptide bridges. Accordingly, as used herein, the term "muramyl peptide" refers to peptidoglycan fragments or subunits containing at least one muramyl residue linked to a peptide. In one embodiment, the muramyl peptide, or a derivative or an analog or a salt thereof, is part of a peptidoglycan or fragment thereof. Thus, in one embodiment, the muramyl peptide may comprise muramic acid and an amino acid.

The glycan chain of peptidoglycan is composed of alternating residues of N-acetylglucosamine and N-acetylmuramic acid linked by β-1,4-glycosidic bonds. Muramic acid has a lactyl side chain on carbon 3 through which the glycan chains are covalently linked to the peptides. Muramic acid residues in different bacterial species may have different side chains at different carbon atoms. For example, many species have an N-acetyl group at carbon 2 and some species do not; and some species have a 1-6-anhydro linkage. Thus, in one embodiment, the muramic acid of the present disclosure may comprise an N-acetyl group. In another embodiment, the muramic acid does not comprise an N-acetyl group.

The amino acid in the muramyl peptide of the present disclosure may include, but is not limited to any amino acids found in bacterial peptidoglycan. In one embodiment, the amino acid in the muramyl peptide of the present disclosure may include proteinogenic amino acid and/or non-proteinogenic amino acid. In one embodiment, the proteinogenic amino acid may include, but is not limited to arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan; the non-proteinogenic amino acid may include, but is not limited to homoserine, lanthionine, ornithine, iso-glutamine, diaminobutyric acid, a-amino-n-butyric acid, norvaline, valine, norleucine, alloisoleucine, t-leucine, α-amino-n-heptanoic acid, pipecolic acid, α,β-diaminopropionic acid, α,γ-diaminobutyric acid, allothreonine, homocysteine, β-alanine, β-amino-n-butyric acid, β-aminoisobutyric acid, γ-aminobutyric acid, α-aminoisobutyric acid, isovaline, sarcosine, N-ethyl glycine, N-isopropyl glycine, N-methyl alanine, N-ethyl alanine, N-methyl β-alanine, N-ethyl β-alanine, isoserine, α-hydroxy-γ-aminobutyric acid and mesodiaminopimelic acid. In one embodiment, the amino acid in the muramyl peptide of the present disclosure may include, but is not limited to alanine, isoglutamine, glutamic acid, diaminobutyric acid, mesodiaminopimelic acid, glycine, homoserine, lanthionine, lysine, ornithine, serine and a salt thereof. In one embodiment, the amino acid in the muramyl peptide of the present disclosure may include, but is not limited to alanine, isoglutamine, glutamic acid, and a salt thereof.

In one embodiment, any of the amino acids may be provided as either an L-amino acid or a D-amino acid. As used herein, "L-amino acids" and "D-amino acids" refer to the two isomers that can occur in every amino acid. "L-amino acids" refer to the amino acid isomer which are manufactured in cells and incorporated into proteins. "D-amino acids" refers to isomeric modification to the amino acid as described herein. In one embodiment, the amino acid in the muramyl peptide of the present disclosure may be provided in an L-D, L-D-L-D, L-D-L-D-L-D, L-D-L-D-L-D-L-D, L-D-L-D-L-D-L-D-L-D, or L-D-L-D-L-D-L-D-L-D-L-D amino acid formation.

In one embodiment, the muramyl peptide may comprise or consist of two amino acids and may be referred to "muramyl dipeptide". Thus, muramyl dipeptide comprises a muramic acid and a dipeptide. The term "dipeptide" as used herein refers to a string of amino acid that consists of two amino acids covalently linked to one another. As used herein, the string of amino acids covalently linked to the muramyl acid may be called peptide bridges. When the muramyl peptide is a muramyl dipeptide, the amino acid may comprise or consist of L-alanine or a salt thereof, and D-isoglutamine or a salt thereof. In another embodiment, the amino acid may comprise or consist of L-alanine or a salt thereof, and D-glutamic acid or a salt thereof.

In another embodiment, the muramyl peptide may comprise or consist of three amino acids and may be referred to as "muramyl tripeptides". In one embodiment of a muramyl tripeptide, the amino acid may comprise or consist of L-alanine or a salt thereof, D-isoglutamine or D-glutamate or a salt thereof, and L-lysine or mesodiaminopimelic acid or a salt thereof.

In another embodiment, the muramyl peptide may comprise or consist of four amino acids and may be referred to as "muramyl tetrapeptides". In one embodiment, the first amino acid of the peptide chain of a muramyl peptide may be an L-alanine. The second in the sequence may be a D-amino acid, for example D-isoglutamine or D-glutamate. The third amino acid may be linked to the γ-carboxyl group of the second amino acid instead of the conventional α-carboxyl group found in proteins. Thus, the third amino acid may be an L-diamino acid such as L-lysine or mesodiaminopimelic acid (mDAP). The fourth amino acid may be a D-alanine. Thus, the peptide chain of the muramyl peptide of the present disclosure may be L-D-L-D sequence, unlike the all L-amino acid sequence of proteins.

In yet another embodiment, the muramyl peptide may comprise or consist of five, six, seven, eight, nine, ten, 11, 12, 13, 14, 15 or more amino acids. As known in the art, the muramyl peptide may comprise or consist of a linear or a branched peptide. For example, a tetrapeptide from parallel peptidoglycan chains may be covalently linked between the D-alanine at the end of one peptide and the mDAP from the other peptide, which extends the length of peptide to seven with a one-amino acid (D-ala) branch. In some embodiments, there may be provided a 5-glycine linker joining the D-alanine and mDAP extending the length of the peptide to 11 with a D-alanine branch.

Advantageously, the antibody of the present disclosure may be capable of binding to the muramyl peptide as a whole; for example, the antibodies of the present disclosure may be capable of binding to the muramic acid, the amino acid or the dipeptide as a group. Additionally, in contrast to the common general knowledge of N-acetyl group of muramic acid being an important antigenic determinant, the antibody of the present disclosure may bind to a muramyl peptide with or without N-acetyl group. In one embodiment, the antibody of the present disclosure may bind to a muramyl peptide and not to any of its subcomponents such as alanine, glutamic acid, iso-glutamic acid, muramic acid, or N-acetyl muramic acid. Without wishing to be bound by theory, it is envisaged that the ability of the antibody of the present disclosure to only bind muramyl peptides, and not to its subcomponents, provides the antibody its high specificity for muramyl peptides and peptidoglycan. Thus, in one embodiment, the antibody of the present disclosure may be capable of binding to the muramyl peptide, or a derivative or an analog or a salt thereof, that includes, but is not limited to N-acetylmuramyl-L-alanyl-D-isoglutamine, muramyl-L- alanyl-D-isoglutamine, N-acetylmuramyl-L-alanyl-D-glutamate, muramyl-L-alanyl-D-glutamate and the like.

An example of the antibody of the present disclosure includes E27, which comprises a heavy chain encoded by the nucleotide sequence of ATGCTGGTGGAGTCTGGGGGAGGCTTGGTGCAACCTGGAGGATCCATGAAACTCT CCTGTATAGTCTCGGGATTTACTTTCAGTTATTATTGGATGTCTTGGGTCCGCCAGTCTCCAGAGAAGGGGTTTGAGTGGGTTGCTGAAATCAGATTGAAATCTGAGAATTA TGCAACAAATTATACGGAGTCTGTGAAAGGGAAGTTCACCATCTCAAGAGATGAT TCCAAAAGTCGTCTCTACCTGCAAATGAACAGCTTAGGAGCTGAGGACACTGGAA TTTATTACTGTCTAACTGGTTATGCCTGGTTTGCTTATTGGGGCCAAGGGACTCTAG TCACTGTCTCTGCAGCCAAAACGACACCCCCATCTGTCTATCCACTGGCCCCTGGA TCTGCTGCCAAACTAACTCCATGGTGACCCTGGGATGCCTGGTCAAGGGCTATTT CCCTGAGCCAGTGACAGTGACCTGGAACTCTGGATCCCTGTCCAGCGGTGTGCAC ACCTTCCCAGCTGTCCTGCAGTCTGACCTCTACACTCTGAGCAGCTCAGTGACTGT CCCCTCCAGCACCTGGCCCAGCGAGACCGTCACCTGCAACGTTGCCCACCCGGCC AGCAGCACCAAG (SEQ ID NO: 1).

In one embodiment, the isolated antibody or an antigen-binding fragment may comprise or consist of a light chain encoded by the nucleotide sequence of GACGTCCAGATGATCCAGTCTCCAAAGCGCCTAATCTATCTGGTGTCTAAACTGGA CTCTGGAGTCCCTGACAGGTTCACTGGCAGTGGATCAGGAACAGATTTTACACTG AAAATCAGCAGAGTGGAGGCTGAGGATTTGGGAGTTTATTACTGCGTGCAACATA CACATTTTCCCACGTTCGGAGGGGGGACCAAGCTGGAAATAAAACGGGCTGATGC TGCACCAACTGTATCCATCTTCCCACCATCCAGTGAGCAGTTAACATCTGGAGGTG CCTCAGTCGTGTGCTTCTTGAACAACTTCTACCCCAAAGACATCAATGTCAAGTGG AAGATTGATGGCAGTGAACGACAAAATGGCGTCCTGAACAGTTGGACTGATCAGG ACAGCAAAGACAGCACCTACAGCATGAGCAGCACCCTCACGTTGACCAAGGACG AGTATGAACGACATAACAGCTATACCTGTGAGGCCACTCACAAGACATCAACTTC ACCCATTGTCAAGAGCTTCAACAGGAATGAGTGT (SEQ ID NO: 2).

In one embodiment, the isolated antibody or an antigen-binding fragment thereof may comprise or consist of a heavy chain encoded by the nucleotide sequence of SEQ ID NO: 1 and a light chain encoded by the nucleotide sequence of SEQ ID NO: 2.

In one embodiment, the isolated antibody or an antigen-binding fragment thereof may comprise or consist of a heavy chain variable domain comprising the amino acid sequence as set in forth MLVESGGGLVQPGGSMKLSCIVSGFTFSYYWMSWVRQSPEKGFEWVAEIRLKSENYA TNYTESVKGKFTISRDDSKSRLYLQMNSLGAEDTGIYYCLTGYAWFAYWGQGTLVTV SAAKTTPPSVYPLAPGSAAQTNSMVTLGCLVKGYFPEPVTVTWNSGSLSSGVHTFPA VLQSDLYTLSSSVTVPSSTWPSETVTCNVAHPASSTK (SEQ ID NO: 3), or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 3, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

In one embodiment, the isolated antibody or an antigen-binding fragment thereof may comprise or consist of a light chain variable domain comprising the amino acid sequence as set forth in DVQMIQSPKRLIYLVSKLDSGVPDRFTGSGSGTDFTLKISRVEAEDLGVYYCVQHTHF PTFGGGTKLEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPIVKSFNR NEC (SEQ ID NO: 4), or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 4, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

In one embodiment, the isolated antibody or an antigen-binding fragment thereof as described herein, may comprise or consist of a heavy chain variable domain comprising the amino acid sequence as set forth in SEQ ID NO: 3, or a variant thereof, and a light chain variable domain comprising the amino acid sequence as set forth in SEQ ID NO: 4, or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 3 or SEQ ID NO: 4, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

"Sequence Identity" as used herein refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods. Methods to determine sequence identity are codified in publicly available computer programs that determine sequence identity between given sequences. Examples of such programs include, but are not limited to, BLASTP, BLASTN and FASTA. The BLASTX program is publicly available from NCBI and other sources. These programs optimally align sequences using default gap weights in order to produce the highest level of sequence identity between the given and reference sequences.

The term antibody also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments). Accordingly, in one embodiment, the isolated antibody or an antigen-binding fragment thereof of the present disclosure may be selected from the group consisting of a humanized antibody and a chimeric antibody.

The term "monoclonal antibody" as used herein refers to a preparation of antibody molecules of single molecular composition. A monoclonal antibody composition displays a single binding specificity and affinity for a particular epitope. The monoclonal antibodies may be generated by a hybridoma which includes a B cell obtained from a transgenic nonhuman animal, such as a transgenic mouse, having a genome comprising a heavy chain transgene and a light chain transgene which encodes the antibody of the present disclosure, fused to an immortalized cell. Thus, in one embodiment, the isolated antibody or an antigen-binding fragment thereof may be a monoclonal antibody.

An antibody of the present disclosure may possess any isotype. Accordingly, in one embodiment, the isolated antibody may be of isotype IgG1, IgG2, IgG3, IgG4, IgD, IgA, IgE, or IgM. In yet another embodiment, the isolated antibody or an antigen-binding fragment thereof may be a monoclonal antibody and may be of the subtype IgG1.

An antibody of the present disclosure may also include fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody; (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment, which consists essentially of a $V_H$ domain and also called domain antibodies; (vi) camelid or nobodies and (vii) an isolated complementarity determining region (CDR). Accordingly, in one embodiment, the antigen-binding fragment may be selected from the group consisting of Fab, Fab', (Fab')$_2$, Fv, sFV, and scFv.

Advantageously, the antibody or antigen-binding fragment may bind to the muramyl peptide, or a derivative or an analog or a salt thereof, with a Kd value significantly less than values known in the art. As used herein, the term "Kd" (M) refers to the dissociation equilibrium constant of a particular antibody-antigen interaction. In one embodiment, the Kd may be selected from the group consisting of less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, and less than about 10 pM. For example, 2E7 mAb, which is one example of the antibody of the present disclosure, has been shown to have picomolar affinity. This is in contrast to other monoclonal antibody known in the art (i.e. mAb2-4), wherein inhibition assays using mAb2-4 showed that 50% inhibition of mAb2-4 binding to peptidoglycan by N-acetylmuramyl-L-alanyl-D-isoglutamine occurred only at concentrations higher than 1 mg/ml. Thus, the antibody of the present disclosure advantageously has higher binding affinity as compared to other known monoclonal antibody.

In a second aspect, there is provided an isolated antibody or an antigen-binding fragment thereof comprising or consisting of a heavy chain variable domain comprising the amino acid sequence as set forth in SEQ ID NO: 3, or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 3, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

In a third aspect, there is provided an isolated antibody or an antigen-binding fragment thereof comprising or consisting of a light chain variable domain comprising the amino acid sequence as set forth in SEQ ID NO: 4, or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 4, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

In a fourth aspect, there is provided an isolated antibody or an antigen-binding fragment thereof comprising or consisting of a heavy chain variable domain comprising the amino acid sequence as set forth in SEQ ID NO: 3, or a variant thereof, and a light chain variable domain comprising the amino acid sequence as set forth in SEQ ID NO: 4, or a variant thereof. The variant may comprise an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO: 3 or SEQ ID NO: 4, whilst still retaining at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody.

Also disclosed are nucleic acid molecules such as DNA sequences, encoding heavy and light chains of an antibody of the present disclosure. Thus, in a fifth aspect, there is provided an isolated nucleic acid molecule that may comprise or consist of SEQ ID NO: 1 or SEQ ID NO: 2.

In a sixth aspect, there is provided a vector comprising the isolated nucleic acid molecule according to the fifth aspect. As used herein the term "vector" may be interchangeably used with "an expression vector", or "a set of expression vectors", encoding an antibody of the present disclosure. The heavy and light chain of the antibody may be encoded by the same vector or by different vector. Such expression vectors may be used for recombinant production of antibodies of the present disclosure. In one embodiment, the expression vector may comprise a nucleotide sequence encoding one or more of the amino acid sequences including, but is not limited to SEQ ID NO: 3 and SEQ ID NO: 4. An expression vector in the context of the present disclosure may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

In a seventh aspect, there is provided a host cell comprising the nucleic acid molecule according to the fifth aspect or the vector according to the sixth aspect. The term "host cell" (or "recombinant host cell"), as used herein, refers to a cell into which an expression vector has been introduced, e.g. an expression vector encoding an antibody as described herein. Recombinant host cells may include, but is not limited to transfectomas, such as CHO (Chinese Hamster Ovary) cells, HEK293 (Human Embryonic Kidney 293 cell line) cells, NS0 (murine myeloma cell line) cells, Per.C6 (human embryonic retinal cell line) cells and BHK (baby hamster kidney) cells and lymphocytic cells.

In an eighth aspect, there is provided an isolated cell line that produces the antibody or an antigen-binding fragment thereof as described herein. In one embodiment, the isolated cell line is an immortal cell line, such as a hybridoma.

In a ninth aspect, there is provided a method of producing an antibody or an antigen-binding fragment thereof as described herein, comprising the steps of culturing the host cell according to the seventh aspect or the isolated cell line according to the eighth aspect under suitable conditions and recovering the antibody or antigen-binding fragment thereof.

In a tenth aspect, there is provided a method of producing an antibody or an antigen-binding fragment thereof as described herein comprising the steps of inoculating a muramyl peptide, or a derivative or an analog or a salt thereof, as described herein into a non-human animal, and isolating antibodies or antigen-binding fragments produced therefrom. In one embodiment, the muramyl peptide, or a derivative or an analog or a salt thereof, may include, but is not limited to N-acetylmuramyl-L-alanyl-D-isoglutamine, muramyl-L-alanyl-D-isoglutamine, N-acetylmuramyl-L-alanyl-D-glutamate, muramyl-L-alanyl-D-glutamate and the like. The non-human animal may include mouse, rabbit, guinea pig, rat, monkey and other suitable animals. In one embodiment, the antibody may be generated by generating the antibody in a transgenic non-human animal. The term "transgenic non-human animal" refers to a non-human animal having a genome comprising one or more human heavy and/or light chain transgenes or transchromosomes (either integrated or non-integrated into the animal's natural genomic DNA) and which is capable of expressing fully the antibody of the present disclosure. For example, a transgenic mouse can have a light chain transgene and either a heavy chain transgene or heavy chain transchromosome, such that the mouse produces anti-muramyl peptides antibody as described herein when immunized with muramyl peptides as described herein and/or cells expressing muramyl peptides.

With increased specificity and affinity, the antibody of the present disclosure may be used as research tools for detection, quantification and neutralization of muramyl peptide in biological samples. Additionally, recent scientific advances linking muramyl peptide to diverse human diseases and the rapid expanding research activities in the area of microbiota and human diseases are creating a high demand for such antibodies. Thus, in an eleventh aspect, there is provided a composition comprising an antibody or an antigen-binding fragment thereof as described herein, and a pharmaceutically acceptable carrier. In one embodiment, the composition may further comprise one or more therapeutic agents. In one embodiment, the therapeutic agent may include, but is not limited to an antimicrobial agent or an antibiotic such as antibacterial agent, antiviral agent and anti-fungal agent, an antineoplastic agent such as a chemotherapeutic agent, a radioisotope, a drug moiety, a nucleolytic enzyme, a lysozyme, a proteinase, a lipase and an immunosuppressant. In one embodiment, the therapeutic agent may be administered separately or together with the antibody of the present disclosure.

In a twelfth aspect, there is provided a vaccine comprising a muramyl peptide, or a derivative or an analog or a salt thereof, as described herein.

The antibody of the present disclosure may also be used as a 'warhead' to specifically deliver other antibacterial agents to bacterial cells to effect targeted killing of pathogens. For example, in a thirteenth aspect there is provided an immunoconjugate comprising an antibody or an antigen-binding fragment thereof as described herein. The immunoconjugate may be covalently attached to: a cytotoxic agent including, but is not limited to antibacterial agent, a chemotherapeutic agent, a drug moiety, an antibiotic, a radioisotope, a nucleolytic enzyme, a lysozyme, a proteinase and a lipase; or a capture label; or a detection label including, but is not limited to fluorescein, rhodamine, dansyl, Lissamine, cyanine, phycoerythrin, Texas Red, and a radionuclide detection label.

As the binding of the antibody of the present disclosure to muramyl peptide block the biological activities of muramyl peptide (for example activation of proinflammatory responses), the antibody of the present disclosure may be developed into therapeutic agents for prevention and treatment of relevant diseases. Accordingly, in a fourteenth aspect, there is provided a method of prophylactically or therapeutically treating an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-associated disorder. The method may comprise administering to a subject an isolated antibody or an antigen-binding fragment thereof as described herein, a composition according to the eleventh aspect, or an immunoconjugate according the thirteenth aspect.

Advantageously, as the antibody as described herein binds to a common structural motif in peptidoglycan, which is a universal component in bacteria, it is envisaged that the antibody as described herein may be used to develop broad-spectrum anti-bacterial agents. Without wishing to be bound by theory, the antibody of the present disclosure may bind to the surface of bacteria cells and contributes to immunity in three ways: antibody coating of bacterial cells prevents pathogens from entering or damaging host cells, stimulates removal of pathogens by macrophages and other immune cells, and triggers destruction of pathogens by stimulating other immune responses such as the complement pathway. Many conventional antibiotics have become obsolete, because the pathogens have developed resistance via various mechanisms including mutational changes of the drug target. The core structure of peptidoglycan, target of the antibody of the present disclosure, has not changed through billions of years of evolution, and is not expected to change to develop resistance to the antibody. Accordingly, in a fifteenth aspect there is provided a method of prophylactically or therapeutically treating a bacterial infection. The method may comprise administering to a subject an isolated antibody or an antigen-binding fragment thereof as described herein, a composition according to the eleventh aspect, or an immunoconjugate according to the thirteenth aspect.

In a sixteenth aspect, there is provided an isolated antibody or an antigen-binding fragment thereof as described herein, a composition according to the eleventh aspect, or an immunoconjugate according to the thirteenth aspect, for use in the prophylactic or therapeutic treatment of an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-associated disorder.

In a seventeenth aspect, there is provided an isolated antibody or an antigen-binding fragment thereof as described herein, a composition according to the eleventh aspect, or an immunoconjugate according to the thirteenth aspect, for use in the prophylactic or therapeutic treatment of a bacterial infection.

In an eighteenth aspect, there is provided use of an isolated antibody or an antigen-binding fragment thereof as described herein, a composition according to the eleventh aspect, or an immunoconjugate according to the thirteenth aspect, in the manufacture of a medicament for prophylactically or therapeutically treating an autoimmune or inflammatory disease selected from the group consisting of sepsis, septic shock, Crohn's disease, rheumatoid arthritis, asthma, allergy, atopic disorders, multiple sclerosis, pertussis, gonorrhea, inflammatory bowel disease, and antibiotic-related disorder.

In a nineteenth aspect, there is provided use of an isolated antibody or an antigen-binding fragment thereof as described herein, a composition according to the eleventh aspect, or an immunoconjugate according to the thirteenth aspect, in the manufacture of a medicament for prophylactically or therapeutically treating a bacterial infection.

Bacterial infections as disclosed herein may include any infections caused by any bacteria. In one embodiment, the bacterial infection may include, but is not limited to a Gram-positive bacterial infection and a Gram-negative bacterial infection. For example, the bacteria may be of a genus including, but not limited to *Acetobacter, Acinetobacter, Actinomyces, Agrobacterium* spp., *Azorhizobium, Azotobacter, Anaplasma* spp., *Bacillus* spp., *Bacteroides* spp., *Bartonella* spp., *Bordetella* spp., *Borrelia, Brucella* spp., *Burkholderia* spp., *Calymmatobacterium, Campylobacter, Chlamydia* spp., *Chlamydophila* spp., *Clostridium* spp., *Corynebacterium* spp., *Coxiella, Ehrlichia, Enterobacter, Enterococcus* spp., *Escherichia, Francisella, Fusobacterium, Gardnerella, Haemophilus* spp., *Helicobacter, Klebsiella, Lactobacillus* spp., *Lactococcus, Legionella, Listeria, Methanobacterium extroquens, Microbacterium multiforme, Micrococcus luteus, Moraxella catarrhalis, Mycobacterium* spp., *Mycoplasma* spp., *Neisseria* spp., *Pasteurella* spp., *Peptostreptococcus, Porphyromonas, Pseudomonas, Rhizobium, Rickettsia* spp., *Rochalimaea* spp., *Rothia, Salmonella* spp., *Serratia, Shigella, Staphylococcus* spp., *Stenotrophomonas, Streptococcus* spp., *Treponema* spp., *Vibrio* spp., *Wolbachia,* and *Yersinia* spp. In one example, the bacterial infection may be caused by bacteria including, but are not limited to *Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaminogenicus (Prevotella melaminogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia* complex, *Burkholderia cenocepacia, Calymmatobacterium granulomatis, Campylobacter coli, Campylobacter fetus, Campylobacter jejuni, Campylobacter pylori, Chlamydia trachomatis, Chlamydophila.* (such as *C. pneumoniae, Chlamydophila psittaci, Clostridium botulinum, Clostridium difficile, Clostridium perfringens, Clostridium tetani), Corynebacterium diphtheriae, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis Peptostreptococcus, Porphyromonas gingivalis, Pseudomonas aeruginosa, Rhizobium Radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis* and *Yersinia pseudotuberculosis.* In one embodiment, the Gram-negative bacterial infection may be an *Escherichia coli* infection. In another embodiment, the Gram-positive bacterial infection may be a *Staphylococcus aureus* infection.

The compositions as described herein may be administered in a number of ways depending upon whether local or systemic treatment is desired. Administration may be topical, pulmonary (e.g., by inhalation or insufflation of powders or aerosols, including by nebulizer; intratracheal, intranasal, epidermal and transdermal) or systemic such as oral, and/or parenteral. Parenteral administration includes intravenous, intraarterial, subcutaneous, intraperitoneal or intramuscular injection or infusion; or intracranial, e.g., intrathecal or intraventricular, administration. In one example, the route of administration may be selected from the group consisting of systemic administration, oral administration, intravenous administration and parenteral administration Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, emulsions, and liposome-containing formulations. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms including, but not limited to tablets, capsules, liquid syrups, soft gels, suppositories, and enemas. The compositions as described herein may also be formulated as suspensions in aqueous, non-aqueous or mixed media. Aqueous suspensions may further contain substances that increase the viscosity of the suspension including, for example, sodium carboxymethyl cellulose, sorbitol and/or dextran. The suspension may also contain stabilizers.

In one embodiment, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions as described herein may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the antibody(s) of the formulation.

The composition as used herein may be provided in a therapeutically effective amount. The term "therapeutically effective amount" as used herein includes within its meaning a sufficient but non-toxic amount of the compound as described herein to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of the composition, and can generally be estimated based on $EC_{50}s$ found to be effective in in vitro and in vivo animal models or based on the examples described herein. In general, dosage is from 0.01 μg to 100 g/kg of body weight, and may be given once or more times daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 μg to 100 g/kg of body weight, once or more times daily, to once every 2 years.

In one example, the compound may be administered in an amount of between any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg per kg of body weight of the subject.

In one example, the concentration of the administered compound is about 1 to about 100 mg/Kg of body weight of the subject, about 5 to about 100 mg/Kg of body weight of the subject, about 10 to about 100 mg/Kg of body weight of the subject, about 20 to about 100 mg/Kg of body weight of the subject, about 30 to about 100 mg/Kg of body weight of the subject, about 1 to about 50 mg/Kg of body weight of the subject, about 5 to about 50 mg/Kg of body weight of the subject and about 10 to about 50 mg/Kg of body weight of the subject.

As used herein, the term "about", in the context of amounts or concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

In one embodiment, the subject may be an animal, mammal, human, including, without limitation, animals classed as bovine, porcine, equine, canine, lupine, feline, murine, ovine, avian, piscine, caprine, corvine, acrine, or delphine. In one embodiment, the subject may be a human.

As muramyl peptides have been linked to many diseases, abnormally high levels of these molecules in the human body may predispose a person to certain diseases. The antibody of the present disclosure may provide a powerful tool for establishment of correlations between levels of muramyl peptide in the human body and diseases. Once such correlations are established, diagnostic tools using the antibody of the present disclosure can be developed for relevant diseases. Simple tests of muramyl peptide levels in samples may be incorporated into routine medical examinations for assessment of risks of people developing certain diseases. Thus, in a twentieth aspect, there is provided a method of detecting the presence or absence of a muramyl peptide, or a derivative or an analog or a salt thereof, as described herein, in a sample. The method may comprise contacting the sample with an isolated antibody or an antigen-binding fragment thereof as described herein, a composition according to the eleventh aspect, or an immunoconjugate according to the thirteenth aspect, and analyzing the sample to determine the presence or absence of the binding product of the muramyl peptide, or a derivative or an analog or a salt thereof, and the isolated antibody or an antigen-binding fragment thereof as described herein. As used herein, the term "binding product" refers to a cell, fragment or agent comprising the muramyl peptide as described and/or which may comprise an epitope or antigenic determinant capable of specific binding to the antibody of the present disclosure. In one embodiment, the methods may further comprise comparing the level of the binding product in a biological sample from a subject to the level of the binding product in a control sample, wherein a higher level of the binding product in the biological sample relative to the level of the binding product in the control sample indicates that the subject has or is predisposed to a condition including, but is not limited to autoimmune or inflammatory disease and a bacterial infection. In one embodiment, the method may further comprise comparing the level of the binding product in the sample to the level of the binding product in a control, wherein a higher level of the binding product in the sample relative to the level of the binding product in the control indicates that the sample is contaminated with bacteria.

"Control" as used herein may refer to a reference with known level of binding product and may be a "negative control" and/or a "positive control". A "negative control" refers to a reference that is known to be substantially devoid of any binding product, for example distilled water. A "positive control" refers to a reference that is known to comprise a pre-determined level of the binding product, for example samples containing known amounts of muramyl peptides.

As used herein, the term "sample" refers to any sample, which includes biological sample as well as non-medical related sample. Such samples may, for example, include samples derived from or comprising stool, whole blood, serum, plasma, tears, saliva, nasal fluid, sputum, mucus, ear fluid, genital fluid, nipple exudates, nipple aspirates, breast fluid, milk, colostrum, placental fluid, amniotic fluid, lymph fluids, cystic fluids, perspirate, synovial fluid, ascitic fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material and autopsy samples, e.g. cells or tissues from all suitable organs, e.g. the lung, the muscle, brain, liver, pancreas, stomach, mucosal surface, hair, or skin, frozen sections of tissues taken for histologic purposes, archival samples, explants and primary and/or transformed cell cultures derived from patients tissues. In addition, samples from environmental sources, e.g. water samples, meat or poultry samples, samples from sources of potential contamination etc. may be used. In one embodiment, the sample may be a biological sample including, but is not limited to saliva, whole blood, blood fluids (e.g. serum and plasma), lymph and cystic fluids, sputum, stool, tears, mucus, ascitic fluid, cystic fluid, urine, nipple exudates, nipple aspirates, cells, tissues (e.g. biopsy and autopsy samples), frozen sections of tissues taken for histologic purposes, archival samples, explants and primary and/or transformed cell cultures derived from patients tissues.

It is also envisaged that commercial kits may be developed for rapid detection of bacterial contamination of medical facilities, reagents, and biological products. Thus, in one embodiment, the sample may also include, but is not limited to foodstuff, beverages, biological products (e.g. antitoxins, bacterial and viral vaccines, blood products, and hormonal extracts), laboratory or medical facilities and laboratory or medical reagents.

In a twenty-first aspect, there is provided an assay for detecting a muramyl peptide, or a derivative or an analog or a salt thereof, as described herein, comprising exposing a sample to an antibody or an antigen-binding fragment thereof as described herein, a composition according to the eleventh aspect, or an immunoconjugate according to the thirteenth aspect, and determining the extent of binding of the antibody, or an antigen-binding fragment thereof, the composition or the immunoconjugate to the sample. In one embodiment, as exemplified by the Experimental section below, the assay of the present disclosure, may include, but is not limited to an enzyme-linked immunosorbent assay (ELISA), immunohistochemistry on histological sections, immunofluorescence test, flow cytometry and the like.

In a twenty-second aspect, there is provided a kit for use in a method according to the twentieth aspect, or in an assay according to the twenty-first aspect, comprising an isolated antibody or an antigen-binding fragment thereof as described herein, a composition according to the eleventh aspect, or an immunoconjugate according to the thirteenth aspect, and one or more reagents for determining the presence or absence of the binding product of a muramyl peptide, or a derivative or an analog or a salt thereof, and the isolated antibody or an antigen-binding fragment thereof as described herein.

The reagents that are suitable for measuring a signal may include reagents that may incorporate a detectable label, such as a fluorophore, radioactive moiety, enzyme, biotin/avidin label, chromophore, chemiluminescent label, or the like, or the kits may include reagents for labeling the nucleic acid primers, the nucleic acid probes or the nucleic acid primers and nucleic acid probes for detecting the presence or absence of the muramyl peptide as described herein. The primers and/or probes, calibrators and/or controls can be provided in separate containers or pre-dispensed into an appropriate assay format, for example, into microtiter plates. The kit may further comprise reagents including, but are not limited to reagents for isolating peptides from samples, reagents for positive or negative controls and reagents for assays as described herein. For example, the kits may include reagents used in the Experimental section below.

The kit may further comprise instructions that may be provided in paper form or in computer-readable form, such as a disc, CD, DVD or the like. The kits may optionally include quality control reagents, such as sensitivity panels, calibrators, and positive controls.

The kits can optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

In a twenty-third aspect, there is provided an antibacterial agent comprising an isolated antibody or an antigen-binding fragment thereof as described herein, a composition according to the eleventh aspect, or an immunoconjugate according to the thirteenth aspect.

In a twenty-fourth aspect, there is provided a hybridoma deposited as Wy-Hyb-2E7 under Accession Number No. PTA-13256 in the American Type Culture Collection (ATCC), Manassas, Va., USA.

In a twenty-fifth aspect, there is provided an antibody comprising the variable heavy and variable light domain sequence of the antibody produced by the hybridoma deposited as Wy-Hyb-2E7 under Accession Number No. PTA-13256 in the American Type Culture Collection (ATCC), Manassas, Va., USA.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention will be further, described in greater detail by reference to specific Examples, which should not be construed as in any way limiting the scope of the invention.

Materials and Methods

Muramyl peptides (MPs) are related molecules sharing common structural moieties. In the present disclosure, two types of mouse monoclonal antibodies were developed with one recognizing a common structure and another specific for subtypes. To achieve this, the following muramyl dipeptides (MDPs) were used as antigens: N-acetylmuramyl-L-alanyl-D-isoglutamine, muramyl-L-alanyl-D-isoglutamine, N-acetylmuramyl-L-alanyl-D-glutamate, and muramyl-L-alanyl-D-glutamate. These MDPs were chemically synthesized or purified from partial HCl-hydrolysis products of N-acetylmuramyl-L-alanyl-D-isoglutamine as described previously (Xu et al., 2008, Bacterial peptidoglycan triggers *Candida albicans* hyphal growth by directly activating the adenylyl cyclase Cyr1p. Cell Host & Microbe 4, 1-12, the content of which is incorporated herewith by reference).

To enhance the antigenicity of the MDPs, these molecules were conjugated to the human serum albumin (HSA) using a linker molecule. The carboxylic acid moiety of MDPs was first coupled to N-Boc-ethylenediamine, and then the Boc protection group was removed and the resulting amine was linked to HSA with glutaraldehyde. Successful conjugation of MDPs to HSA was determined by mass spectrometry. The MDP-HSA conjugates were then used to immunize BALB/c mice. Serum antigen-specific titers of the immunized mice were examined by enzyme-linked immunosorbent assay (ELISA) against MDPs conjugated to ovalbumin (OVA) using the same linkage strategy as described above. Generation of hybridoma cell lines, screening of antibody-producing clones, preparation and purification of mAbs, and mAb isotyping were carried out by following standard protocols. Antigen specificity of a mAb was determined using competitive ELISA to test the ability of different MDPs and constituent moieties to inhibit the binding of a mAb to the MDP originally used as antigen for immunization.

Example 1

Characterization of a mAb Against MDPs

A mAb (2E7) was obtained from immunization of mice with N-acetylmuramyl-L-alanyl-D-isoglutamine. Antibody isotyping tests identified 2E7 as IgG$_1$ and the Kd of 2E7 for N-acetylmuramyl-L-alanyl-D-isoglutamine was calculated to be 8.7 pM (FIG. 1). By competitive ELISA, the binding of 2E7 to N-acetylmuramyl-L-alanyl-D-isoglutamine conjugated to OVA was found to be inhibited in a concentration dependent manner by muramyl-L-alanyl-D-isoglutamine, N-acetylmuramyl-L-alanyl-D-glutamate, and muramyl-L-alanyl-D-glutamate almost as effectively as N-acetylmuramyl-L-alanyl-D-isoglutamine, indicating that 2E7 recognizes a common epitope in the four MDPs. However, 2E7 did not exhibit detectable affinity to muramic acid, N-acetylmuramic acid, N-acetylglucosamine, alanine, D-isoglutamine, glutamate, glucose, or any or a mixture of the 20 common amino acids in proteins at concentrations 100 times higher than their normal concentrations in the blood. The data indicate that 2E7 specifically recognizes an epitope formed uniquely in a structural context common in the four MDPs. An IgG$_1$ mAb that specifically recognizes the glutaraldehyde linker used to couple MDP to HSA was also obtained in the screening of hybridoma clones. This antibody exhibited no detectable affinity to any of the above molecules except glutaraldehyde, providing an excellent negative control for experiments using 2E7.

Example 2

Determination of the Amino Acid Sequences of the Variable Region of the Heavy and Light Chains of 2E7

Messenger RNAs were prepared from the hybridoma clone that produces 2E7 and then used as templates to produce complementary DNA. The DNA fragment encoding the variable region of the heavy and light chain respectively was amplified by polymerase chain reactions (PCR) using pairs of oligonucleotide primers (Table 1) specifically targeting conserved sequence motifs flanking the coding region for the variable region (method of which is described in Kettleborough et al., 1993, Optimisation of primers for cloning libraries of mouse immunoglobulin genes using the polymerase chain reaction. Eur J Immunol 23, 206-211 and Pope et al., 1996, Construction of use of antibody gene repertoires. In Antibody Engineering—A Practical Approach. Edited by McCafferty J. Hoogenboom H, and Chiswell D., the content of both are incorporated herewith by reference). The PCR products were purified, spliced into the pJET1.2/blunt vector (Fermentas International Inc, Canada) and transformed into Escherichia coli to obtain independent clones. Plasmids were isolated from multiple clones and the ones with an insert of the expected size were subjected to DNA sequence analysis. Five clones each for heavy and light chains were analyzed, which yielded identical sequences. The nucleotide sequences were then translated into amino acid sequences (Table 2). Their identity as the variable region of the heavy or light chain of mouse antibodies was confirmed by using the sequences to search the NCBI non-redundant protein sequence database. The 2E7 heavy chain sequence exhibited the highest identity of 75-90% to dozens of mouse antibodies over the same region, and the 2E7 light chain sequence exhibited identities up to 98%. No identical sequence in the database was found to either the heavy or light chain of 2E7.

TABLE 1

Oligonucleotide primers for PCR amplification of the DNA coding sequence for the variable region of the heavy and light chain of 2E7.

Heavy chain primers

Forward
1.   5'-ATGCTGGTGGAGTCTGGGGGA-3'(SEQ ID NO: 5)
2.   5'-AAGCTGGTGGAATCTGGAGGA-3'(SEQ ID NO: 6)
Reverse
     5'-CTTGGTGCTGCTGGCCGGGTG-3'(SEQ ID NO: 7)

Light chain primers

Forward
1.   5'-CCGTTTGATTTCCAGCTTGGTGCC-3' (SEQ ID NO: 8)
2.   5'-CCGTTTCAGCTCCAGCTTGGTCCC-3' (SEQ ID NO: 9)
Reverse
     5'-GACATTGAGCTCACCCAGTCTCCA-3' (SEQ ID NO: 10)

TABLE 2

Nucleotide and amino acid sequences of the variable regions of 2E7

Heavy chain (208 amino acids) (SEQ ID NO: 3):
MLVESGGGLVQPGGSMKLSCIVSGFTFSYYWMSWVRQSPEKGFEWVAEI
RLKSENYATNYTESVKGKFTISRDDSKSRLYLQMNSLGAEDTGIYYCLT
GYAWFAYWGQGTLVTVSAAKTTPPSVYPLAPGSAAQTNSMVTLGCLVKG
YFPEPVTVTWNSGSLSSGVHTFPAVLQSDLYTLSSSVTVPSSTWPSETV
TCNVAHPASSTK Nucleotide sequence (624 nucleotides)
(SEQ ID NO: 1):
ATGCTGGTGGAGTCTGGGGGAGGCTTGGTGCAACCTGGAGGATCCATGA
AACTCTCCTGTATAGTCTCGGGATTTACTTTCAGTTATTATTGGATGTC
TTGGGTCCGCCAGTCTCCAGAGAAGGGGTTTGAGTGGGTTGCTGAAATC
AGATTGAAATCTGAGAATTATGCAACAAATTATACGGAGTCTGTGAAAG
GGAAGTTCACCATCTCAAGAGATGATTCCAAAAGTCGTCTCTACCTGCA
AATGAACAGCTTAGGAGCTGAGGACACTGGAATTTATTACTGTCTAACT
GGTTATGCCTGGTTTGCTTATTGGGGCCAAGGGACTCTAGTCACTGTCT
CTGCAGCCAAAACGACACCCCCATCTGTCTATCCACTGGCCCCTGGATC
TGCTGCCCAAACTAACTCCATGGTGACCCTGGGATGCCTGGTCAAGGGC
TATTTCCCTGAGCCAGTGACAGTGACCTGGAACTCTGGATCCCTGTCCA
GCGGTGTGCACACCTTCCCAGCTGTCCTGCAGTCTGACCTCTACACTCT
GAGCAGCTCAGTGACTGTCCCCTCCAGCACCTGGCCCAGCGAGACCGTC
ACCTGCAACGTTGCCCACCCGGCCAGCAGCACCAAG Light chain (177 amino acids) (SEQ ID NO: 4):
DVQMIQSPKRLIYLVSKLDSGVPDRFTGSGSGTDFTLKISRVEAEDLGV
YYCVQHTHFPTFGGGTKLEIKRADAAPTVSIFPPSSEQLTSGGASVVCF
LNNFYPKDINVKWKIDGSERQNGVLNSWTDQDSKDSTYSMSSTLTLTKD
EYERHNSYTCEATHKTSTSPIVKSFNRNEC Nucleotide sequence (531 nucleotides)
(SEQ ID NO: 2):
GACGTCCAGATGATCCAGTCTCCAAAGCGCCTAATCTATCTGGTGTCTA
AACTGGACTCTGGAGTCCCTGACAGGTTCACTGGCAGTGGATCAGGAAC
AGATTTTACACTGAAAATCAGCAGAGTGGAGGCTGAGGATTTGGGAGTT
TATTACTGCGTGCAACATACACATTTTCCCACGTTCGGAGGGGGGACCA
AGCTGGAAATAAAACGGGCTGATGCTGCACCAACTGTATCCATCTTCCC
ACCATCCAGTGAGCAGTTAACATCTGGAGGTGCCTCAGTCGTGTGCTTC
TTGAACAACTTCTACCCCAAAGACATCAATGTCAAGTGGAAGATTGATG
GCAGTGAACGACAAAATGGCGTCCTGAACAGTTGGACTGATCAGGACAG
CAAAGACAGCACCTACAGCATGAGCAGCACCCTCACGTTGACCAAGGAC
GAGTATGAACGACATAACAGCTATACCTGTGAGGCCACTCACAAGACAT
CAACTTCACCCATTGTCAAGAGCTTCAACAGGAATGAGTGT Example 3

Figure 2:
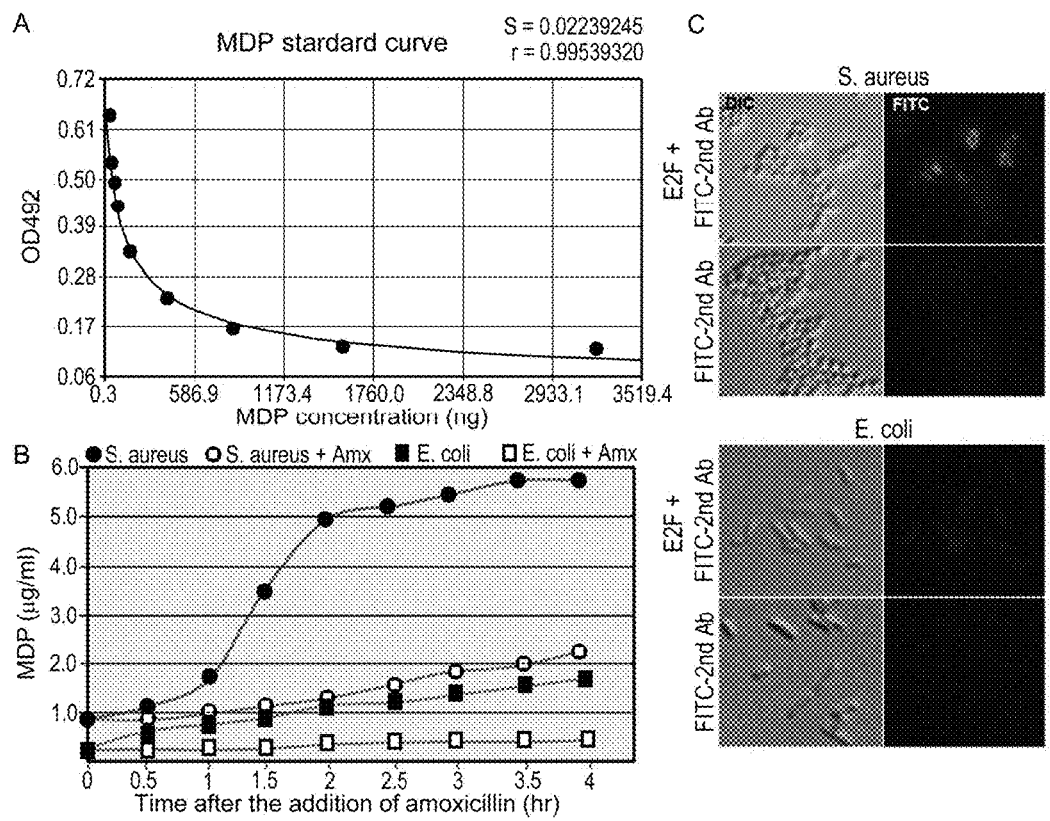
FIG. 2 (A) shows a standard curve that was generated by fitting N-acetylmuramyl-L-alanyl-D-isoglutamine concentrations and $OD_{492}$ values to the Shifted Power Fit equation $y=a*(x-b)\char`\^c$ using CurveExpert Basic. The standard curve was used to determine the peptidoglycan concentration in a sample. (B) shows a graph showing Staphylococcus aureus and Escherichia coli growth in liquid LB medium in the presence or absence of amoxicillin. Both bacteria were grown to $OD_{600}$=1.5. Each culture was divided into two, and one treated with 40 μg/ml amoxicillin (Amx) and the other untreated. Aliquots were collected at the indicated times and the amount of MPs in the supernatant was determined by competitive ELISA. (C) shows fluorescence microscope images of Staphylococcus aureus and Escherichia coli after incubation with 2E7. Both Staphylococcus aureus and Escherichia coli live cells were first washed with phosphate buffered saline (PBS) 3 times and then incubated with 2E7. After removing unbound antibodies by PBS washes, the cells were incubated with a FITC-labeled anti-mouse IgG Ab before fluorescence microscopic examination.

2E7 Detection of Bacterial Peptidoglycan in Culture Medium and on the Cell Surface To demonstrate the utility of 2E7, the antibody was first tested on its ability to detect MPs that are normally present in bacterial cultures. It is well established that β-lactam antibiotics inhibit peptidoglycan polymerization by causing cells to accumulate and secrete MPs. β-lactam antibiotic amoxicillin, which is a drug commonly used in hospitals, were added to the culture and a significant increase in the substance that can inhibit 2E7 binding to N-acetylmuramyl-L-alanyl-D-isoglutamine was expected to increase. For this test, Gram-positive bacterium *Staphylococcus aureus*, which has a thick peptidoglycan layer, and Gram-negative *Escherichia coli*, which has a thin peptidoglycan layer, were selected and grown in the presence or absence of amoxicillin. The culture was grown to a density of $OD_{600}=1.5$ and then divided into two equal aliquots. To one aliquot, amoxicillin was added to a final concentration of 40 μg per ml, and to the other aliquot, no drug was added. Both cultures were allowed to continue to grow. Aliquots of cultures were collected at timed intervals and cells were removed by centrifugation. The amount of MPs in the supernatant was determined by competitive ELISA using 2E7. We found that the addition of amoxicillin caused a sharp increase in the culture medium of molecules that can effectively inhibit 2E7 binding to N-acetylmuramyl-L-alanyl-D-isoglutamine (FIG. 2A-B). In comparison, only a slow, gradual increase of such molecules was observed in untreated cultures. Furthermore, supernatant of the *Staphylococcus aureus* culture exhibited ~15 times stronger inhibition than that of the *Escherichia coli* culture. As a negative control, none of the supernatants discernibly inhibited the binding of the control antibody against glutaraldehyde under otherwise identical conditions.

The ability of 2E7 in binding to peptidoglycan in the cell wall was also investigated. Both *Staphylococcus aureus* and *Escherichia coli* cells were first incubated with 2E7 and then with an anti-mouse IgG Ab conjugated with FITC. Fluorescence microscopy examination revealed strong staining of *Staphylococcus aureus* and weak staining of *Escherichia coli* cells (FIG. 2C), consistent with their respective level of peptidoglycan content in the cell wall. Incubation with the secondary FITC-Ab alone resulted in only faint non-specific staining. Furthermore, incubating 2E7 but not the control antibody with live *Staphylococcus aureus* or *Escherichia coli* caused significant cell aggregation (data not shown), indicating cross-linking of bacterial cells by 2E7. Taken together, the data indicate that the antibody of the present disclosure, 2E7, specifically recognizes peptidoglycan in bacterial cell wall and MPs released in bacterial cultures.

Example 4

Influence of Amoxicillin on the MP Level in the Blood in Mice and Humans

Figure 3:
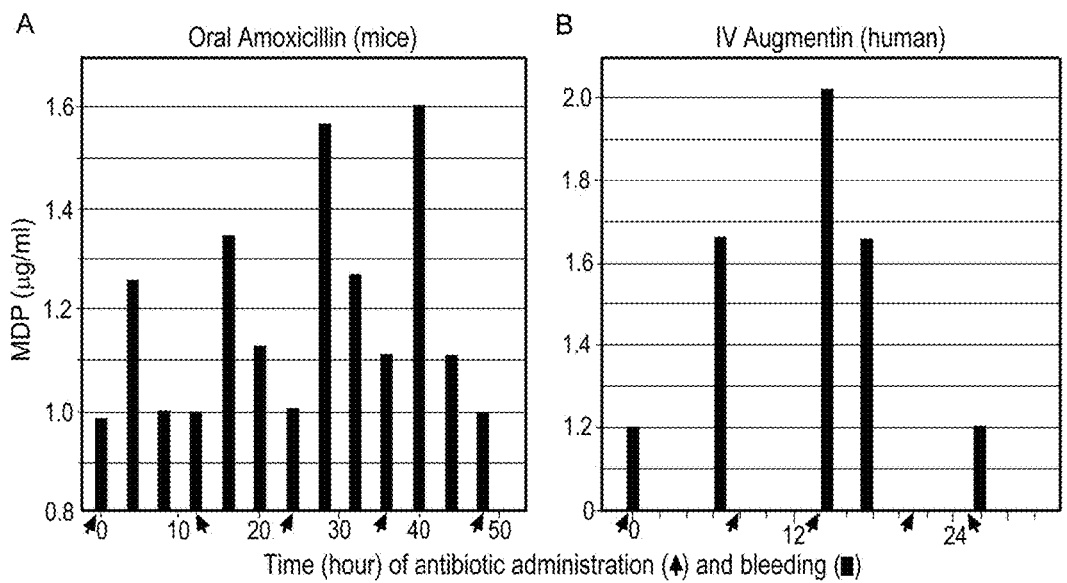
FIG. 3 (A) shows a bar graph of the results of ELISA on the study of amoxicillin administration into mice. Amoxicillin was administered orally to 50 mice at 12-h intervals and three mice were sacrificed every 4 h to collect blood for peptidoglycan quantification by ELISA. (B) shows a bar graph of the results of ELISA on blood samples from a human patient who received multiple IV injections of Augmentin. Serial blood samples were taken. Time for blood draw and IV injection are indicated.

To determine whether β-lactam antibiotics treatment of mice would cause a sudden increase in the blood MP level, which can occur as a result of inhibition of peptidoglycan synthesis in bacteria of the mouse microbiota, mice were fed with amoxicillin (100 mg/kg) at 12-h intervals and three mice were sacrificed every 4 h to collect blood for a period of three days. The MP level in serum was determined by competitive ELISA using an example of the antibody of the present disclosure, i.e. 2E7. As shown in FIG. 3A, the serum of untreated mice (0 h) contains a level of MPs equivalent to ~1 μg/ml of N-acetylmuramyl-L-alanyl-D-isoglutamine. Strikingly, a 20-60% increase in the blood MP level was observed at 4 h after each antibiotic feeding, although the level returned to the basal level during the next few hours until the next feeding.

At the same time, blood samples from an ICU patient who received multiple IV administration of Augmentin (amoxicillin clavulanate, a β-lactamase inhibitor reducing amoxicillin degradation by bacterial β-lactamase) was obtained serially at 0, 7.5 h, 14 h, 21 h, and 26 h. The blood sample taken before the antibiotic treatment contained an amount of MPs equivalent to ~1.2 μg/ml of N-acetylmuramyl-L-alanyl-D-isoglutamine (FIG. 3B). As shown in FIG. 3B, the MP level increased to 1.66 and 2.1 μg/ml in samples taken at 6.5 and 13.5 h. In contrast, the MP level lowered to 1.68 and 1.2 μg/ml at 17 and 26 h. These results indicate that the use of β-lactam antibiotics indeed causes a significant increase of MPs in the blood. These results might explain the cause of some antibiotic-associated diseases such as diarrhea as a consequence of MP-induced excessive inflammation in the gut. The data also suggest the presence of regulatory mechanisms in mice and humans that can effectively restore the blood MPs to the homeostatic state level in response to MP fluctuations in the body.

Example 5

Detection and Quantification of Blood MPs in Healthy People

Figure 4:
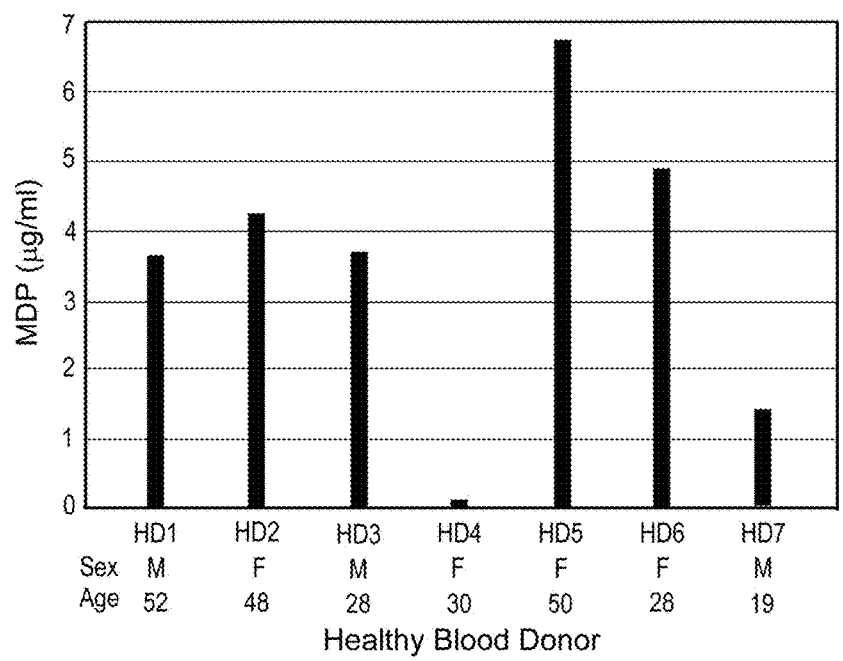
FIG. 4 shows the detection and quantification of PG subunits in healthy donors. Blood was taken from seven generally healthy donors and the level of peptidoglycan in the serum was determined by competitive ELISA using E2F. The sex and age of the donors are shown.

It was hypothesized that due to genetic and/or environmental factors, MPs levels in individuals may vary. Since MPs have a diverse range of biological activities and have been linked to numerous diseases, the blood level of MPs may be used as a biomarker for assessment of risks of individuals for developing certain diseases. As a first step, the MP level in generally healthy people was determined. Blood samples and prepared serum from seven voluntary donors, four female and three male aged from 19 to 52 at 10:00 am of the same day (FIG. 4) were collected. Strikingly, the serum MP level was found to vary over a wide range. One serum (HD4) contained a barely detectable amount of MPs, while the highest MP concentration detected was 6.82 μg/ml (HD5). The levels of MPs in the rest of the serum samples ranged from 1.4 to 4.94 μg/ml. When blood samples were obtained again from HD4 and HD5 two weeks later, similar results were observed. From another independent group of four donors, a second serum sample was found to contain an undetectable level of MPs. The data indicate that the blood MP level indeed exhibits significant inter-individual variations. Incidentally, the two donors with the highest blood peptidoglycan levels, HD5 and HD6, particularly HD5, have chronic inflammation-related skin problems and often need to take antibiotics for extended periods of time for anti-inflammation purposes. The observed correlation between high blood MP levels and the skin problem suggests that the high MP level may be the cause of or contribute to chronic, low grade inflammation.

Monoclonal antibodies raised against N-acetylmuramyl-L-alanyl-D-isoglutamine are known in the art. One such antibody mAb2-4, isotype IgG2a, has been characterized in detail are known in the art. So far, in literature mAb2-4 has been used only in immunostaining of tissues to detect the presence of peptidoglycan mainly in inflammatory tissues and macrophages. However, there has been no report of applying this antibody to detect peptidoglycan or MPs in solution by ELISA. mAb2-4 were found to have very low affinity to MPs. Inhibition assays using mAb2-4 showed that 50% inhibition of mAb2-4 binding to peptidoglycan by N-acetylmuramyl-L-alanyl-D-isoglutamine occurred only at concentrations higher than 1 mg/ml, which is significantly lower than the picomolar affinity of the antibody of the present disclosure, 2E7 mAb.

Additionally, structural analysis of antigenic determinant showed that the mAb2-4 antibody recognizes the N-acetylmuramic acid linked to the dipeptide but not N-acetylmuramic acid or the dipeptide alone and that the N-acetyl group on muramic acid is an important antigenic determinant. Thus, the antigenic determinant on N-acetylmuramyl-L-alanyl-D-isoglutamine for mAb2-4 is different from that for the antibody of the present disclosure, (e.g. 2E7) which recognizes MDPs with or without the N-acetyl group. As many bacterial species do not have the N-acetyl group in the muramic acid residue, it follows that mAb2-4 has narrower specificity than 2E7 in recognizing bacterial species.

Another rather commonly used mouse monoclonal antibody for peptidoglycan is mAb2E9. This antibody was developed by immunizing mice with partially purified peptidoglycan-polysaccharide complexes isolated from feces of a healthy human. The affinity of this antibody to N-acetylmuramyl-L-alanyl-D-isoglutamine was found to be even lower than mAb2-4, and the antigenic determinant has not been defined. mAb2E9 has been used in immunostaining of tissues but never in ELISA.

Other monoclonal antibodies developed by immunizing mice with peptidoglycan isolated from *Streptococcus mutans* have also been described. Although these antibodies could recognize peptidoglycan prepared from multiple bacterial species including both Gram-positive and gram-negative ones, the binding could not be inhibited by N-acetylmuramyl-L-alanyl-D-isoglutamine and the antigenic determinant is not known.

In summary, currently available mouse monoclonal antibodies developed against either N-acetylmuramyl-L-alanyl-D-isoglutamine or peptidoglycan have limited use because of low affinity, poorly defined antigenic determinant and narrow specificity. None of these antibodies can be used to detect peptidoglycan or MPs in solution at sensitivity levels required by most research and clinical needs.

As shown in the present disclosure, 2E7 mAb can detect MPs with picomolar affinity. Furthermore, 2E7 recognizes an epitope universally present in all bacterial species. The antigenic determinant is formed with structural contributions from multiple molecular moieties and structural features only found in bacteria, ensuring the high specificity of 2E7 for bacterial peptidoglycan.

The invention claimed is:

1. An isolated antibody or an antigen-binding fragment thereof, capable of binding to a muramyl peptide selected from the group consisting of N-acetylmuramyl-L-alanyl-D-isoglutamine, muramyl-L-alanyl-D-isoglutamine, N-acetyl-muramyl-L-alanyl-D-glutamate, and muramyl-L-alanyl-D-glutamate;
   wherein the isolated antibody or an antigen-binding fragment thereof comprises a heavy chain variable domain comprising the amino acid sequence as set forth in SEQ ID NO: 3, and a light chain variable domain comprising the amino acid sequence as set forth in SEQ ID NO: 4.

2. The isolated antibody or an antigen-binding fragment thereof according to claim 1, comprising a heavy chain encoded by the nucleotide sequence of SEQ ID NO: 1.

3. The isolated antibody or an antigen-binding fragment thereof according to claim 1, comprising a light chain encoded by the nucleotide sequence of SEQ ID NO: 2.

4. The isolated antibody or an antigen-binding fragment thereof according to claim 1, comprising a heavy chain encoded by the nucleotide sequence of SEQ ID NO: 1 and a light chain encoded by the nucleotide sequence of SEQ ID NO: 2.

5. The isolated antibody or an antigen-binding fragment thereof according to claim 1, wherein said antibody or antigen-binding fragment binds to said muramyl peptide, or a derivative or an analog or a salt thereof, with a Kd value selected from the group consisting of less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, and less than about 10 pM.

6. The isolated antibody or an antigen-binding fragment thereof according to claim 1, covalently attached to:
   a cytotoxic agent selected from the group consisting of an antibacterial agent, a chemotherapeutic agent, a drug moiety, an antibiotic, a radioisotope, a nucleolytic enzyme, a lysozyme, a proteinase and a lipase; or
   a capture label; or
   a detection label selected from the group consisting of fluorescein, rhodamine, dansyl, Lissamine, cyanine, phycoerythrin, Texas Red, and a radionuclide detection label, in the form of an immunoconjugate.

7. The isolated antibody or an antigen-binding fragment thereof according to claim 1, as an antibacterial agent.

8. A hybridoma deposited as Wy-Hyb-2E7 under Accession Number No. PTA-13256 in the American Type Culture Collection (ATCC), Manassas, VA, USA.

9. The isolated antibody or an antigen-binding fragment thereof according to claim 1, comprising the variable heavy and variable light domain sequence of the antibody produced by the hybridoma deposited as Wy-Hyb-2E7 under Accession Number No. PTA-13256 in the American Type Culture Collection (ATCC), Manassas, VA, USA.

* * * * *